(12) United States Patent
Foster et al.

(10) Patent No.: US 6,491,637 B2
(45) Date of Patent: Dec. 10, 2002

(54) OPHTHALMOLOGICAL ULTRASONOGRAPHY SCANNING APPARATUS

(75) Inventors: Mark Leighton Foster; Scott Howard Phillips, both of Victoria; Paul Wesley Taylor, Sidney, all of (CA); Dan Reinstein, London (GB)

(73) Assignee: Ultralink Ophthalmics Inc., Vancouver (CA)

( * ) Notice: Subject to any disclaimer, the term of this patent is extended or adjusted under 35 U.S.C. 154(b) by 0 days.

(21) Appl. No.: 09/914,924

(22) PCT Filed: Jan. 5, 2001

(86) PCT No.: PCT/CA01/00008

§ 371 (c)(1),
(2), (4) Date: Jan. 15, 2002

(87) PCT Pub. No.: WO01/49181

PCT Pub. Date: Jul. 12, 2001

(65) Prior Publication Data

US 2002/0169491 A1 Nov. 14, 2002

(30) Foreign Application Priority Data

Jan. 6, 2000 (CA) ............................................ 2.295.431

(51) Int. Cl.⁷ .................................................. A61B 8/00
(52) U.S. Cl. ...................................... 600/452; 600/437
(58) Field of Search .................................. 600/166, 167, 600/437, 170, 174, 180, 452, 451

(56) References Cited

U.S. PATENT DOCUMENTS

| 5,293,871 A | * | 3/1994 | Reinstein et al. | ............ 600/442 |
| 5,331,962 A | * | 7/1994 | Coleman et al. | ............ 600/444 |
| 5,626,594 A | * | 5/1997 | Smith | ........................ 606/166 |

* cited by examiner

Primary Examiner—Francis J. Jaworski
Assistant Examiner—Maulin Patel

(57) ABSTRACT

An apparatus for ultrasound scanning of the eye is provided comprising a virtual center translocation mechanism that facilitates precise arcuate motion of an ultrasonic transducer to maintain focal distance from the eye and to maintain normality of the ultrasound beam with surfaces of the eye. The invention also provides a radius adjust mechanism for changing the radius of ultrasound scanning to facilitate positioning of the transducer focal point on selected surfaces of the eye. Centration optics are also provided, for aligning the ultrasound transducer with the Purkinje (or other optical or geometric) axis of a patient's eye.

17 Claims, 10 Drawing Sheets

OPHTHALMOLOGICAL ULTRASONOGRAPHY SCANNING APPARATUS

FIELD OF THE INVENTION

The invention is in the field of medical ultrasound apparatus, particularly apparatus for use in ultrasonography of the eye.

BACKGROUND OF THE INVENTION

Ultrasound may be used in a variety of medical applications, including diagnostic ultrasonography of the eye. Diagnostic information is typically provided by an ultrasound pulse from a piezoelectric transducer, which is directed into a tissue. Reflected acoustic energy is detected (as 'echoes'), so that the amplitude of the received energy may be correlated with the time delay in receipt of the echo. The amplitude of the echo signal is proportional to the scattering strength of the refractors in the tissue, and the time delay is proportional to the range of the refractors from the transducer. A variety of hand-held ultrasound instruments for measuring corneal thickness (called pachymeters) have been developed (for example see U.S. Pat. Nos. 4,564,018; 4,817,432; 4,930,512). Many prior art ultrasonic pachymeters provide A-scan output, in the form of waveforms displayed on a cathode ray tube, representing acoustic reflections in a single dimensional 'column' of tissue.

In B-scan ultrasonography, a two-dimensional image is formed, in which pixel brightness reflects the amplitude of the reflected acoustic signal. A B-scan image therefore represents a cross-sectional slice of the imaged tissue. The cross-sectional information is typically provided by correlating information from a series of adjoining columnar scans (each of which may be used to produce A-scan output). For the purpose of producing B-scans, adjoining columnar scans may be produced by a number of methods: rectilinear translocation of a transducer over the tissue of interest; pivoting angular displacement of a single transducer over a fan-shaped area; or through the use of a linear array of transducers.

In some applications, three dimensional images may be reconstructed from a series of B-scans. U.S. Pat. No, 4,932,414 to Coleman et al. for example describes a system in which the transducer is electronically swept or physically rotated to produce a series of sectored (fan-shaped) scan planes which are separated by a known angular distance, to produce a 3-dimensional display. In a similar fashion, U.S. Pat. No. 5,487,388 to Rello et al. discloses an ultrasonic scanning system in which sequential fan-shaped B-scan image planes are obtained by movement of the transducer probe in an arc, a movement which allows the apex of the scanned 3-dimensional volume to be located below the probe to facilitate imaging between closely-spaced surface obstructions.

The structure of the eye, particularly the cornea, presents special problems for optimal ultrasonographic B-scan imaging. The human cornea is an asphere, flattening concentrically, typically approximately 11 mm across with an average central radius of curvature of 7.8 mm which increases towards the periphery. The high resolution required for ultrasonic imaging of some corneal structures is optimally achieved if ultrasound data is collected from the focal point of the transducer, and the ultrasound beam is normal to the surface of the cornea. As a result, rectilinear scanning of the cornea provides optimal imaging information only from relatively small segments of the cornea which are normal to the transducer beam and in the plane of beam focus. Similarly, volumetric 3-dimensional scanning by reconstruction of a series of fan-shaped B-scan planes, as for example described in U.S. Pat. Nos. 4,932,414 and 5,487,388, is not a system adapted to provide the degree of resolution required for biometry of the corneal surface.

High frequency ultrasound has been used in ophthalmological ultrasonography to obtain biometric B-scan images of the human cornea, by arcuate translocation of a single element focused transducer. Silverman et al., 1997, J. Ultrasound Med. 16:117–124, describe a system for sonographic imaging and biometry of the cornea in which a sophisticated programmable motion system permits ultrasonographic arc scanning. In the Silverman et al system, the ultrasonic transducer is translated through an arc matched to the approximate radius of curvature of the cornea using five servo motors and a controller. Similarly, U.S. Pat. No. 5,331,962 discloses an ultrasound system for corneal arc scanning, in which a transducer is translocated along a curved track that approximates the surface curvature of the cornea

SUMMARY OF THE INVENTION

In one aspect of the invention, an apparatus for ultrasound scanning of the eye is provided comprising a virtual center translocation mechanism that facilitates precise arcuate motion of an ultrasonic transducer to maintain focal distance from the eye and to maintain normality of the ultrasound beam with surfaces of the eye. The arcuate movement of the transducer focal path may closely approximate the surface of the cornea. Some embodiments of the invention may include a radius adjust mechanism for changing the radius of ultrasound scanning, to accommodate different eye sizes and to facilitate positioning of the ultrasound transducer focal point on selected surfaces of the eye, such as the cornea. Centration optics may also be provided, for aligning the translocation path of the ultrasound transducer with an axis such as, but not limited to, the Purkinje axis of a patient's eye.

In one embodiment, the invention provides an ultrasound transducer support comprising a transducer mount adapted to accommodate an ultrasound transducer having a focal point. The support may be provided with a virtual center mechanism attached to the transducer mount, for moving the ultrasound transducer along an arcuate translation path. The arcuate translation path of the transducer may be offset from a virtual center of translocation by a radius of transducer translocation, so that the focal point of the ultrasound transducer traverses an arcuate focal path about the virtual center of translocation. A radius adjust mechanism may be provided for adjusting the position of the transducer mount to change the radius of transducer translocation.

In an alternative embodiment, the invention provides a method of ophthaamological ultrasonography comprising centring an ultrasound transducer having a focal point in alignment with the Purkinje or other optical or geometric axis of a patient's eye using centration optics, and moving the ultrasound transducer along an arcuate translation path intersecting the Purkinje or other optical or geometric axis of the patient's eye. The arcuate translation path of the transducer may be offset from a virtual center of translocation by a radius of transducer translocation, so that the focal point of the ultrasound transducer traverses an arcuate focal path about the virtual center of translocation.

DETAILED DESCRIPTION OF THE INVENTION

Figure 1A:
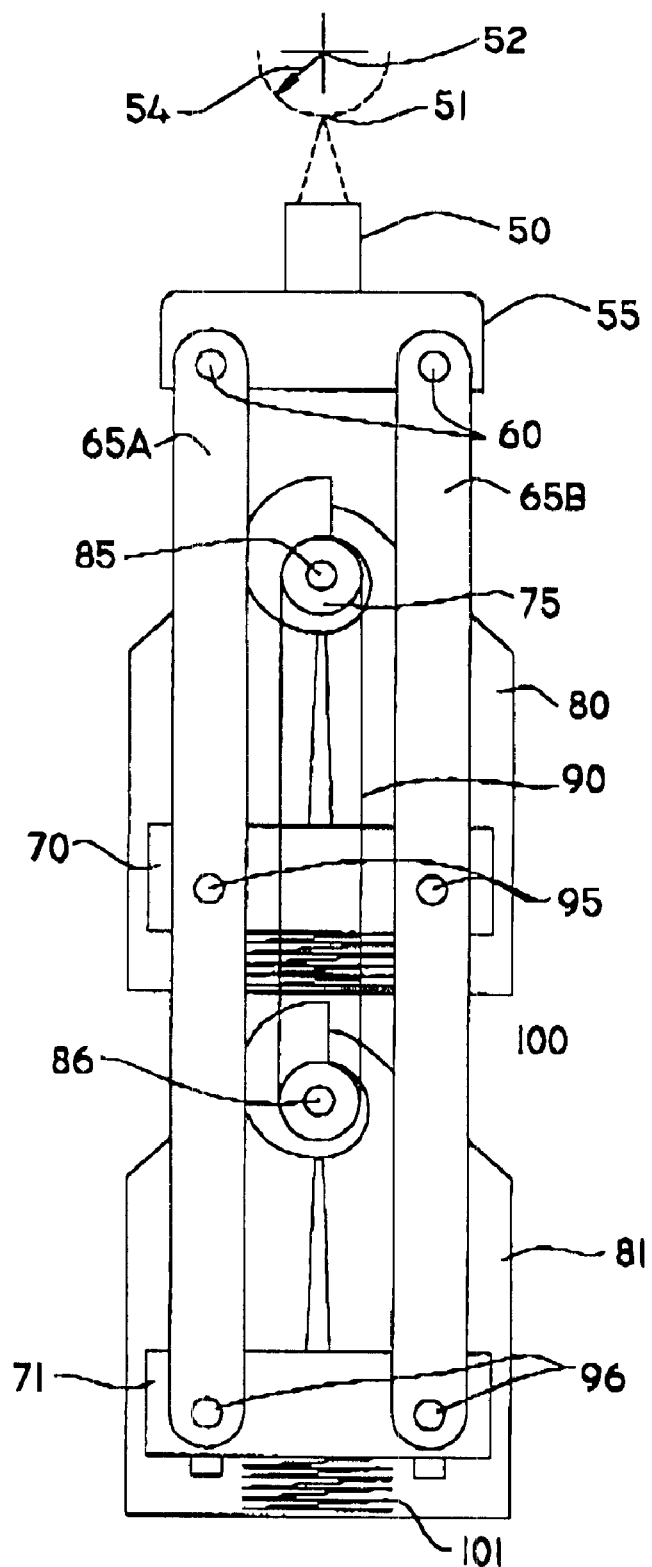
FIG. 1A is a side elevational view of an ultrasound transducer support of the invention, showing a cam-actuated radius adjust mechanism.
Figure 1B:
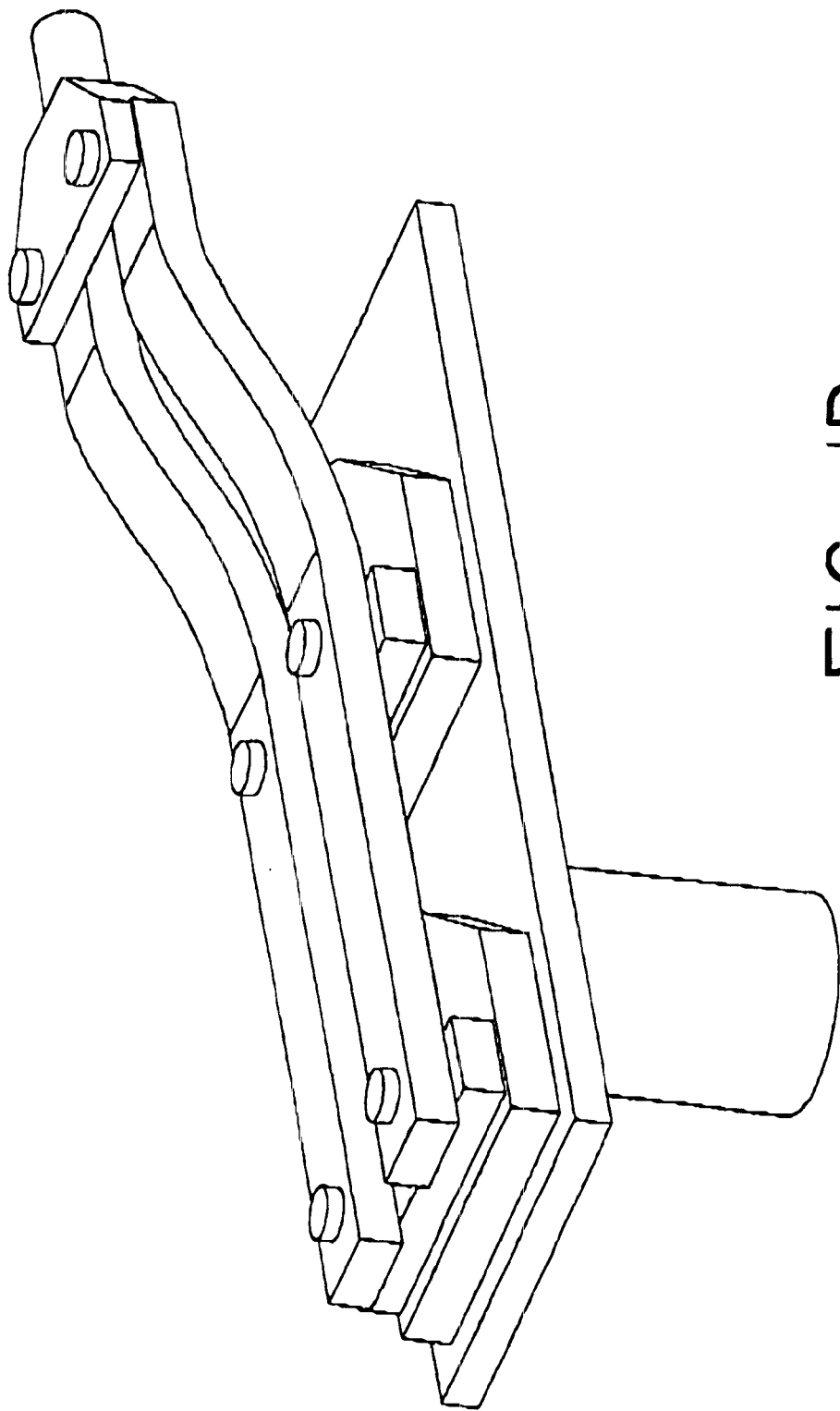
FIG. 1B is an isometric view of an alternative embodiment of the ultrasound transducer support of the invention, showing shaped arm linkages, as are also shown in FIG. 4.

In one aspect, the invention provides an ultrasound transducer support comprising a transducer mount adapted to accommodate an ultrasound transducer, and a virtual center mechanism. FIG. 1A illustrates an embodiment of a virtual center mechanism. First and second arm linkages 65A and 65B are each connected via three pivots to moving parts of the mechanism. Rear swinging pivots 96 connect first and second arm linkages 65A and 65B to rear radius adjust slider 71, and rear radius adjust slider 71 is attached to rear swinging linkage 81. Similarly, front swinging pivots 95 connect arm linkages 65A, 65B to front radius adjust slider 70, and front radius adjust slider 70 is attached to front swinging linkage 80. The front ends of the arm linkages 65A, 653 are connected by transducer pivots 60 to transducer mount 55, and transducer mount 55 is adapted to accommodate ultrasonic transducer 50. Front pivot 85 and rear pivot 86 are stationary relative to the swinging motion of front swinging linkage 80 and rear swinging linkage 81.

Figure 2:
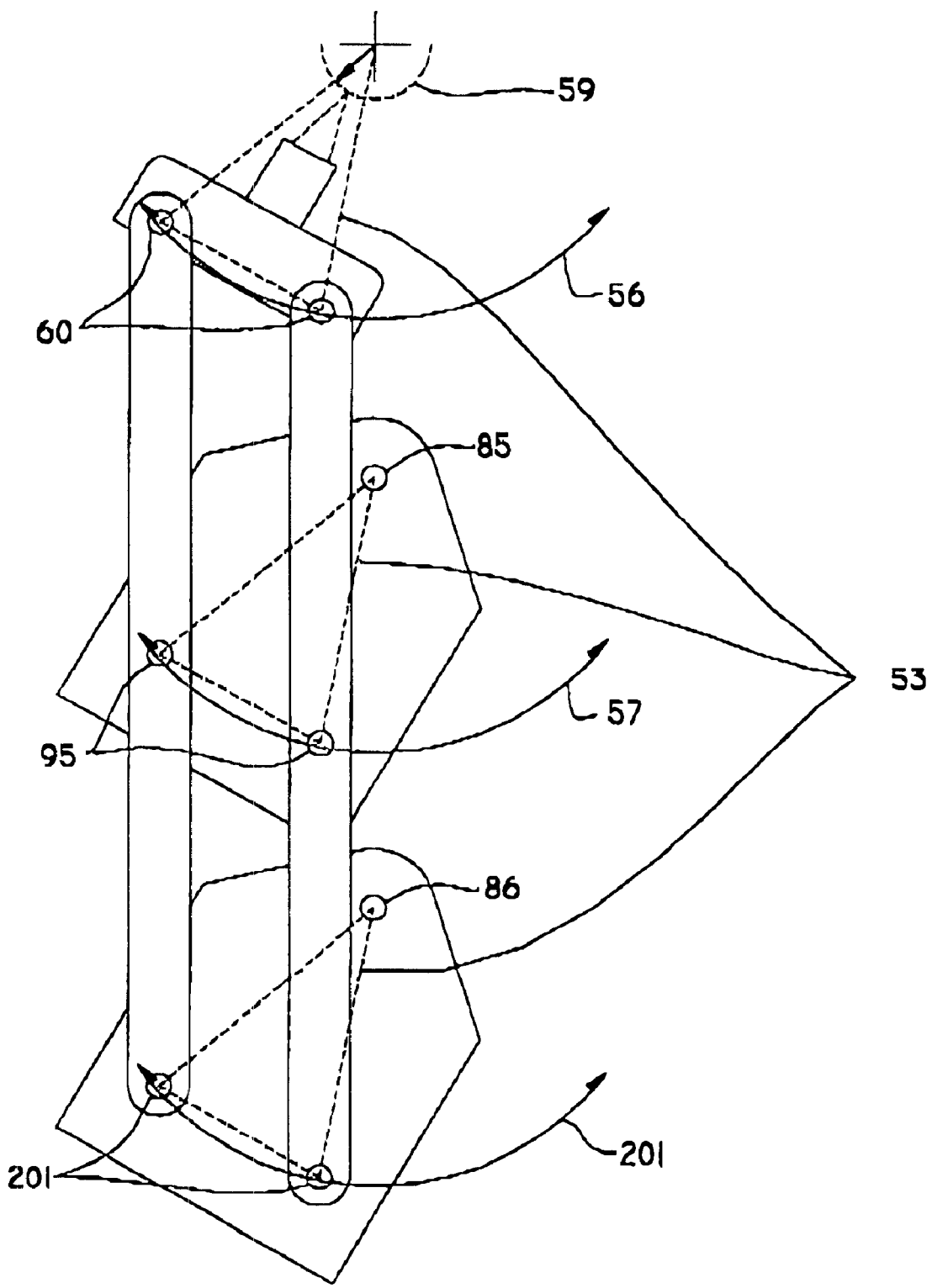
FIG. 2 is a schematic diagram showing the motion of the transducer support of the invention.
Figure 3A:
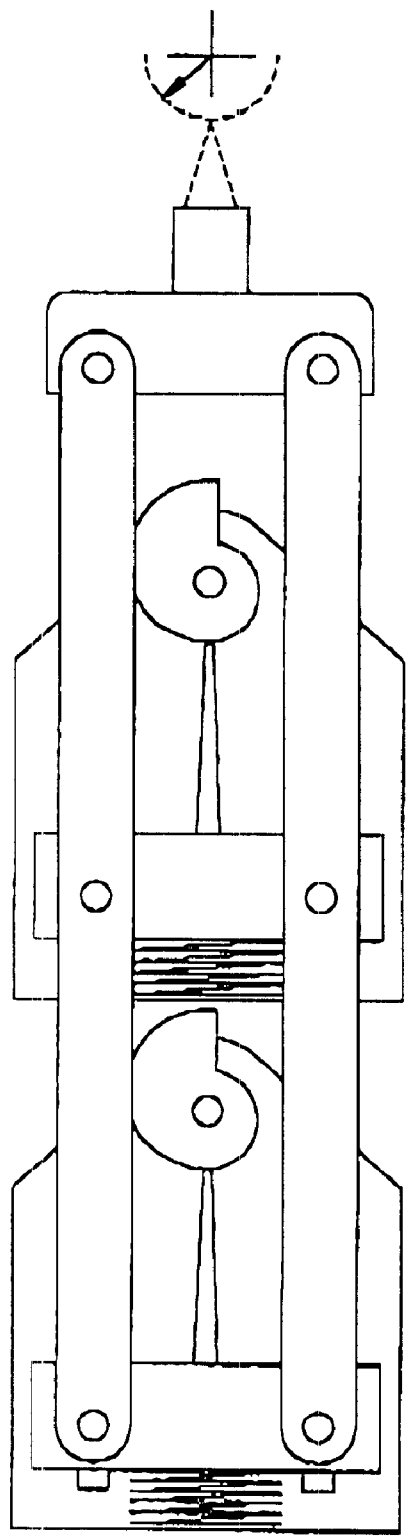
FIGS. 3A and 3B are elevations views of the embodiment of the invention shown in FIG. 1, showing the cams that are part of the radius adjust system in different positions.
Figure 3B:
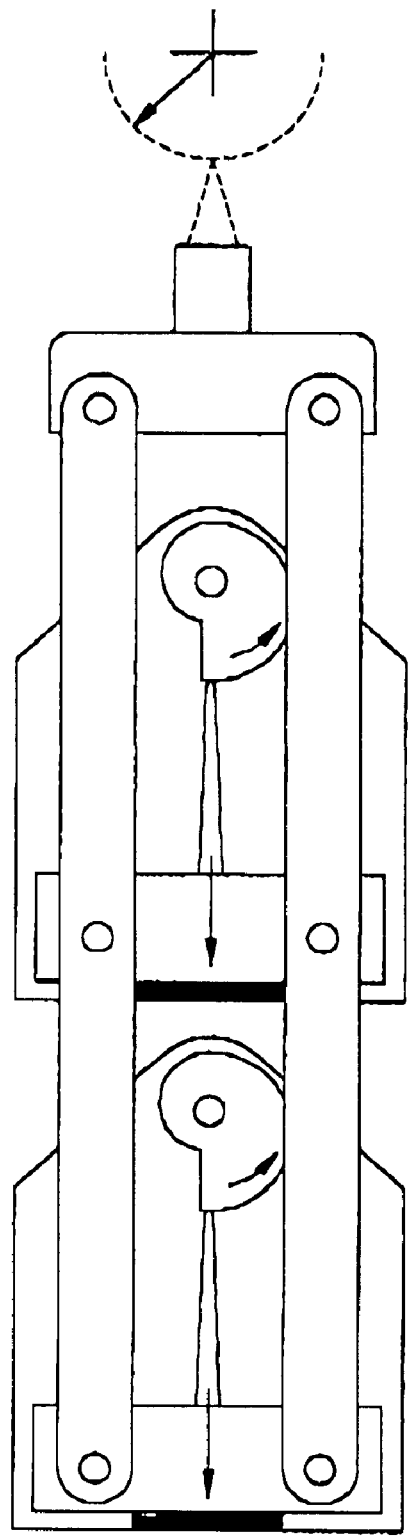

The virtual center mechanism is attached to transducer mount 55 for moving the ultrasound transducer 50 along an arcuate translation path 56 offset from a virtual center of translocation 52 by a radius of transducer translocation, so that the focal point 51 of the ultrasound transducer 50 traverses an arcuate focal path 59 about virtual center of translocation 52. As shown in FIG. 2, when rear swinging linkage 81 rotates about rear pivot 86, rear swinging pivots 96 describe arcuate paths about rear pivot 86. Arm linkages 65A, 65B move front swinging pivots 95, so that front swinging pivots 95 describe identical paths about front pivot 85. Similar triangles 53 show that this swinging motion causes ultrasonic transducer 50 to move in an arc such that its axis pivots about virtual center 52. In addition, transducer focus point 51 traverses an arc 59 about virtual center 52 at image radius 54. The pivoting motion of the apparatus may be driven by scanning driver 82, which may for example be a servo motor. It will be seen that focal point 51 may also lie behind virtual center 52, for example to scan the back of the eye.

The mounting of transducer 50 in transducer mount 55 may be adapted so that the position of transducer 50 is adjustable relative to transducer mount 55. Such an adjustment may be difficult to accomplish during operation, due to the configuration of the assembled apparatus, as shown in FIG. 4. A radius adjust mechanism for adjusting the radius of transducer translocation may be provided, for example by radius adjust sliders 70, 71 which are movable relative to the respective pivot points 85, 86. In operation, the effect of movement of radius adjust sliders 70, 71 is to elongate similar triangles 53. The elongation of triangles 53 reflects simultaneous changes to three radii: a 'first' radius of rotation of front swinging pivots 95; a 'second' radius of rotation of rear swinging pivots 96, and the radius of transducer translocation circumscribed by transducer pivots 60. In addition, image radius 54 is changed (the distance between virtual center 52 and the arcuate focal path 59 traversed by the focal point 51 of transducer 50). The radius adjustment may be driven by rotating radius adjust cams 75, 76 relative to swinging linkages 80, 81. Radius adjust cams 75, 76 may be linked by a rotation linking mechanism, such as anti-backlash belt 90, which operates so that adjusting one cam automatically adjusts the other cam by the same amount. Alternatively, a single cam 75 or 76 could be used on either slider 70 or 71, in which case the other slider would follow. Mechanisms other than cams, such as motors, gears, or other mechanical linkages may be used to actuate sliding movement of radius adjust sliders 70, 71.

Figure 1C:
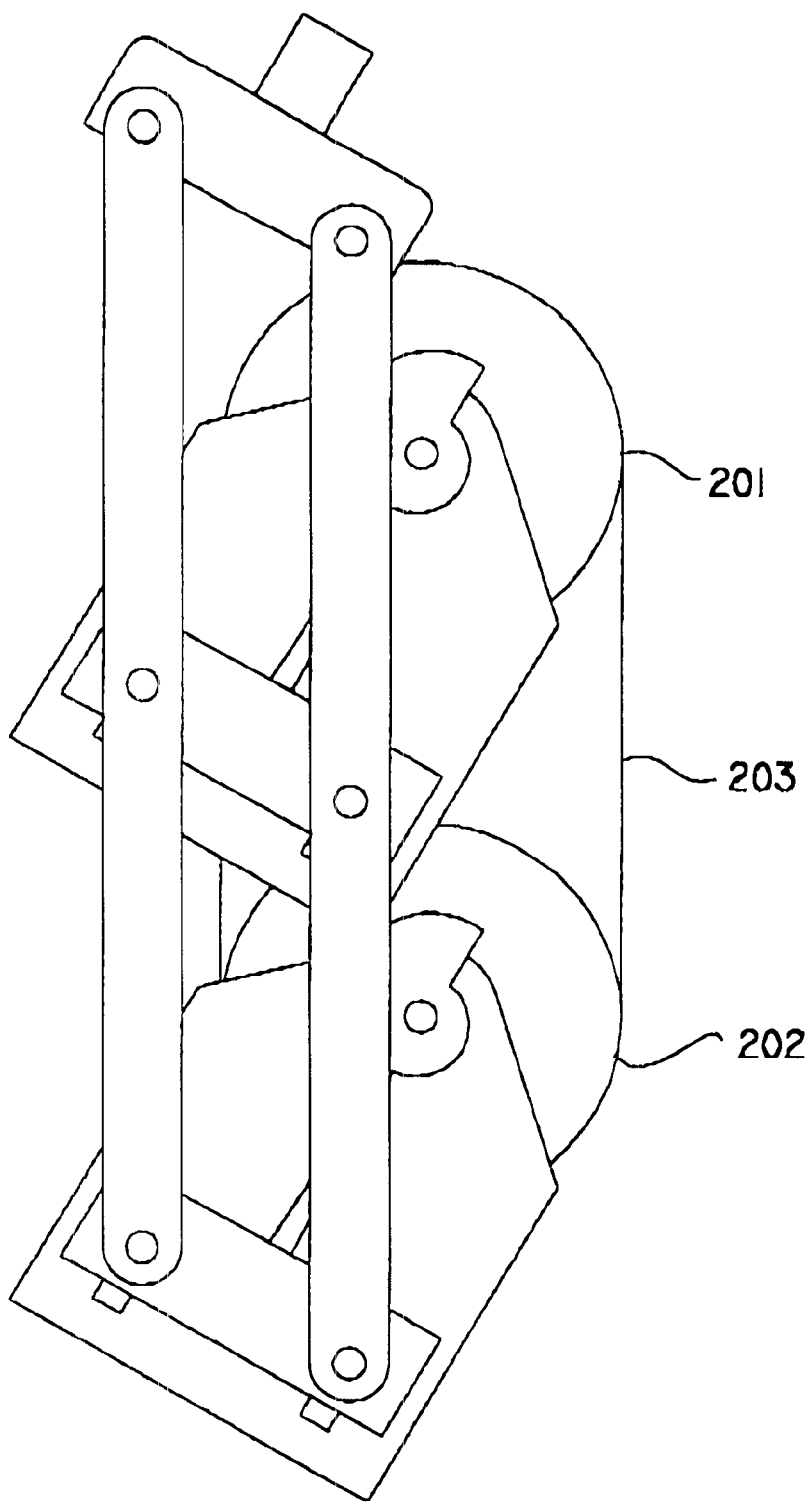
FIG. 1C is a schematic diagram showing a linking element connecting the front and rear swinging linkages which may form part of the transducer part of the invention.

To provide extra rigidity to the mechanism supplementary linking such as that shown in FIG. 1C may be used. Linking element 203 may for example be a steel band or a belt or a chain or a cable and may engage sheaves 201 and 202. Alternatively the linking may be supplied many other ways including driving both swinging linkages 80 and 81 directly with wormgears or flexures.

Figure 4A:
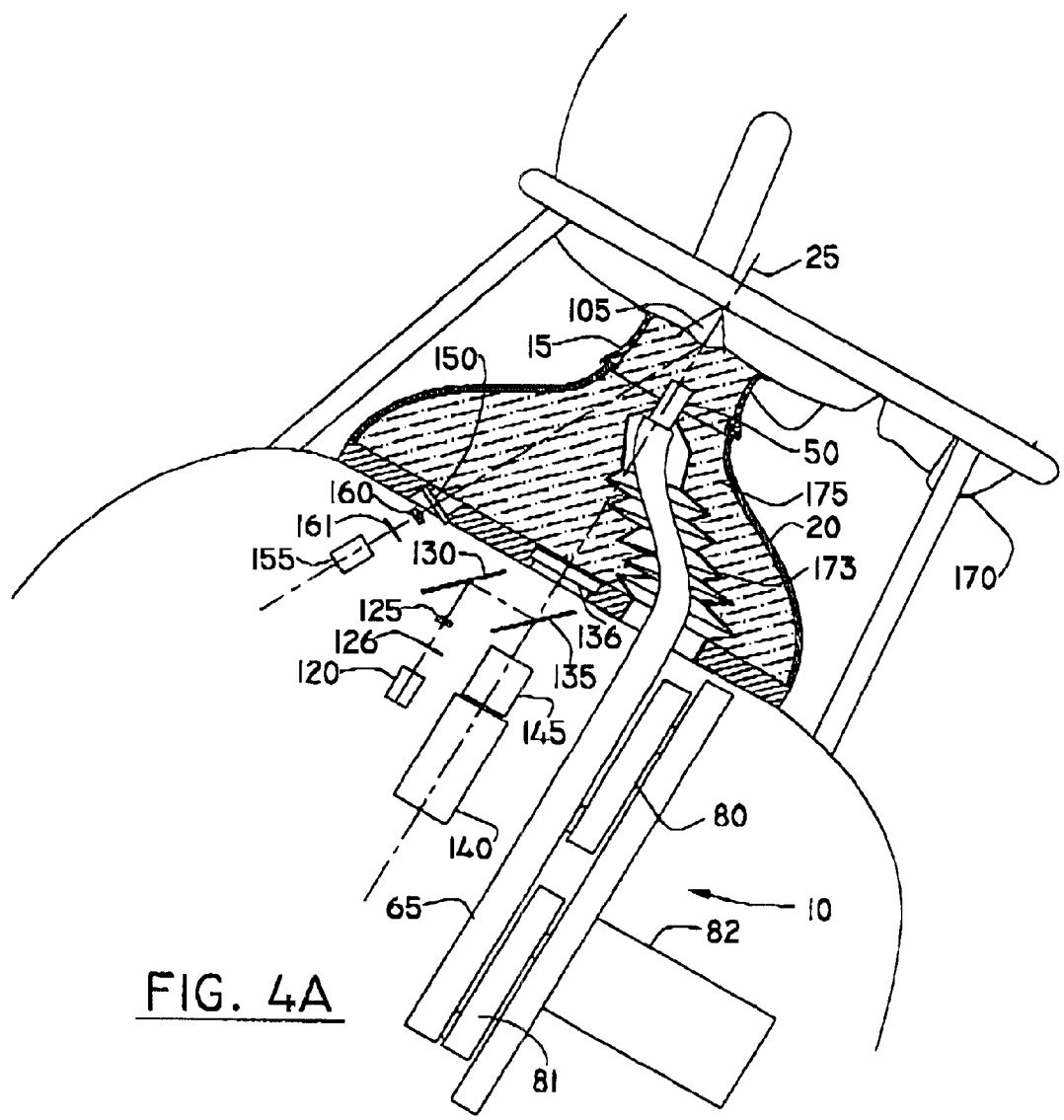
FIG. 4A is a side elevational view showing the ultrasound transducer support of the invention with accessory apparatus for sealing a fluid-filled chamber against the patient's eye.

Ultrasonic transducers for use in accordance with various aspects of the invention may be high frequency transducers, operating for example at frequencies between 50 and 100 MHz. A saline bath may be used to acoustically couple ultrasound transducer 50 to patient's eye 105. FIG. 4A shows the general arrangement of an embodiment of the ultrasound transducer support of the invention with accessory apparatus including a saline bath adapted for diagnostic use. In the illustrated embodiment, a patient may be scanned in a seated position by placing the patient's orbit against eye seal 15. The patient's head may be supported by head support 170 which may be adapted to imnmobilize the patient's head during ultrasound scanning. The overall axis of the apparatus, shown as line 25 in FIG. 4, may be at an angle of about 45 degrees to horizontal. Alternative angles from horizontal to vertical may also be used. In some embodiments, a patient's mandible may be supported with an upward force which encourages the teeth into mechanical contact to stabilize the patient's head. Arranging the apparatus at an overall axis of 45 degrees may help to reduce the accumulation of bubbles in the vacinity of the patient's orbit, particularly when saline fluid fills reservoir 20 and eye seal 15.

Coarse alignment of the eye on axis 25 may be done visually, for example using video camera 140, which preferably has a very high sensitivity. The seal may be tested by slowly filling the saline chamber with saline and watching for leaks. The position of the patient's head may be adjusted, or the eye seal changed, in order to achieve a good seal. Once an acceptable position has been found, the patient's head may be locked into position by immobilizing the head support. With the head stationary the scanning mechanism 10 can be moved relative to saline chamber 15 to make scan axis 25 coincident with the Purkinjie (or other optical or geometric) axis of the patient's eye.

Figure 5:
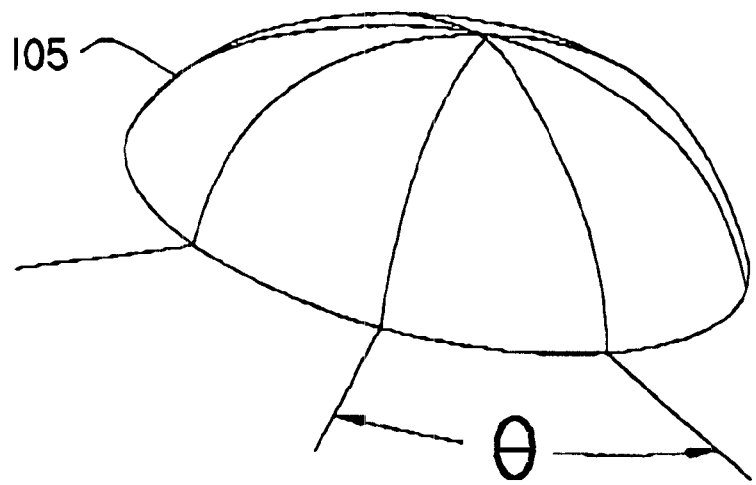
FIG. 5 is a schematic illustration of a series of meridional ultrasound scanning paths which intersect at a point near the apex of the cornea.

In accordance with one aspect of the invention, corneal scanning may be undertaken along a series of meridional paths which intersect at a point near the apex of the cornea, as shown in FIG. 5. In some embodiments, this intersection point may be the Purkinje (or other optical or geometric) axis of the eye, which may be used as an approximation of the optical axis of the eye (defined by the line between the object of regard and the fovea of the retina). The Purkinje axis may be located by shining a focused beam of light into the patient's eye, and examining the Purkinje reflections from four optical surfaces of the eye: the front and rear surfaces of the cornea, and the front and rear surfaces of the lens. The Purkinje reflections are observable along the axis of the light beam. The Purkinje axis is located when the reflections from these four surfaces are coincident. A light beam used to locate the Purkinje axis may also conveniently serve as a view target for the patient. Other axes may be used as an intersection point for meridional scanning such as the vertex-fixation axis. When a light is shone axially toward the eye onto the corneal surface, two reflected images can be seen—the specular (Normal to incident light) reflection and the diffuse reflection (not necessarily Normal reflection). When the position of the light source is adjusted such that the specular and diffuse reflections from the corneal surface are coincident, the light source will now be perpendicular to the vertix of the cornea. The vertex fixation axis is obtained when the patient's eye is looking directly at a fixation target, while observing coincidence of the diffuse and specular corneal surface reflections.

Figure 4B:
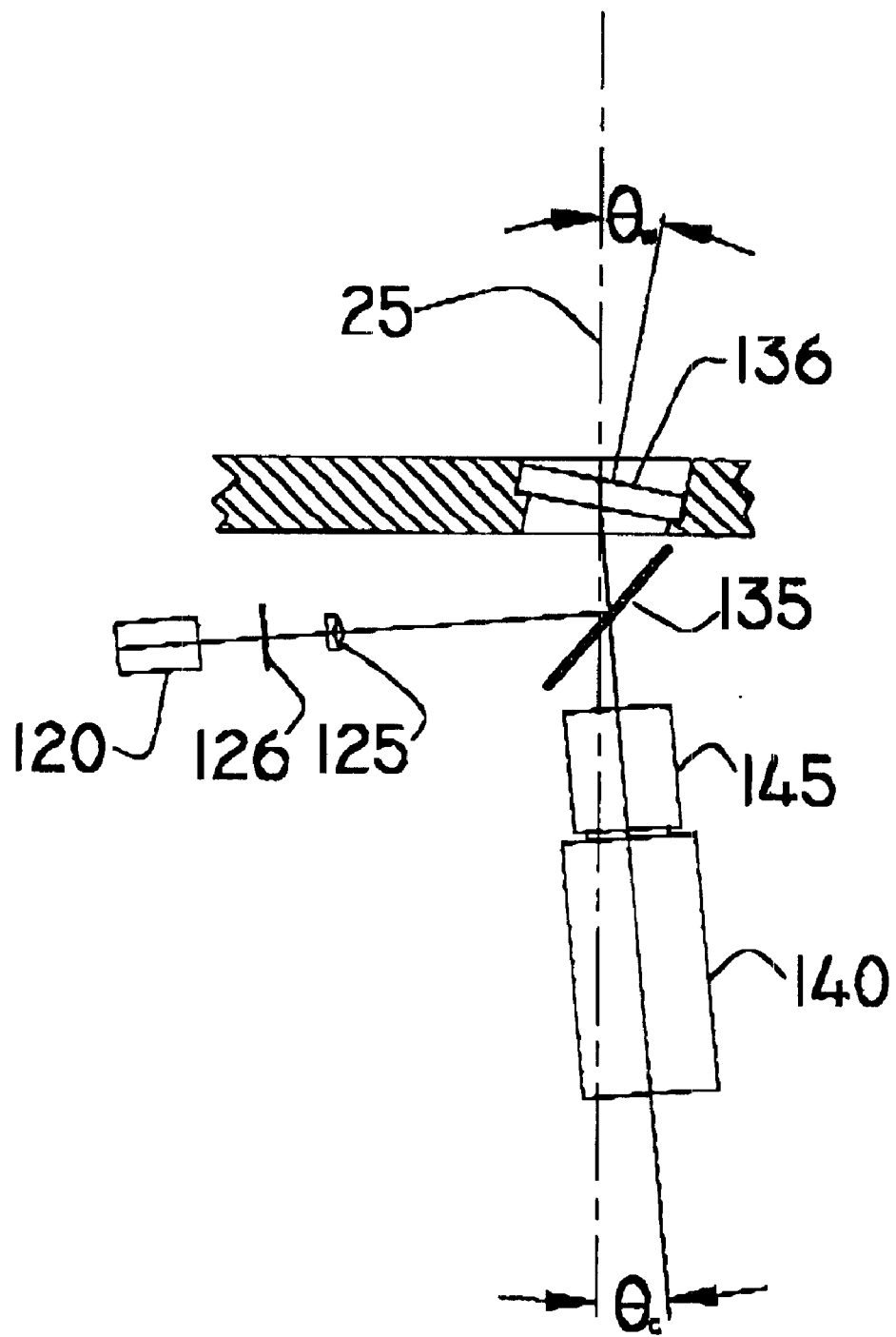
FIG. 4B is a schematic illustration showing alternative optics which may be used in conjunction with methods of centering the transducer using the apparatus of the invention.

FIG. 4A shows an embodiment that includes accessory centration optics for centering the transducer in alignment with the Purkinje axis of the patient's eye. Centration light source 120 may be refined using aperture 126 and focused using centration optics 125. Centration light source 120 may for example be a laser, laser diode, light emitting diode or incandescent source. The centration light beam may be aligned with machine axis 25 using reflector 130, such as a prism or mirror, and beam splitter 135. The centration light beam then passes through fluid-sealed camera window 136 and through the fluid (saline) in cavity 175 before reaching the patient's eye 105. As shown in FIG. 4B in order to address potential back reflection problems from window 136, both camera 140 and window 136 may be tipped relative to machine axis 25 in such a way that the centration beam still travels along the machine axis 25 within the saline chamber 175. The centration light beam thereby intersects the arcuate translation path of transducer 50. The Purkinje reflections then return back through beam splitter 135 and may be recorded by camera 140 through lens 145. As shown in FIG. 4, in order for the light to reach the patient's eye 105, transducer 50 must be swung out to the side as shown in FIG. 2. During an ultrasound scan, because the centration light beam intersects the arcuate translation path of transducer 50, the patient using the centration light as a view target will see the light disappear momentarily as the light is blocked by the passing transducer. This flashing behavior may be helpful in facilitating alignment of the eye, since the photoreceptors in the retina would otherwise saturate after a few seconds of staring at a fixed target light which may cause the eye to shift slightly to compensate.

FIG. 4A also illustrates focus point illuminator 155, which shines through focus point optics 160 and aperture 161 to produce a focus point spot on eye 105. The angle of focus point illuminator 155 is set so that when the focus point spot is appropriately positioned on the eye, the transducer apparatus is in a selected vertical position at a known distance from eye 105. The centration optics may for example be used to determined when the focus point spot joins the Purkinje (or other axis) reflections from the centration light 120. In some embodiments, this positioning of the focus point spot may be used to identify the point at which the apparatus of the invention is positioned at the correct distance from the eye to have the cornea within the focal point of transducer 50.

For extra illumination to improve the eye image on camera 140, an infra-red light may be shone through either of windows 136, 150, in which case the camera will be adapted to be sensitive to the wavelength selected.

Figure 6:
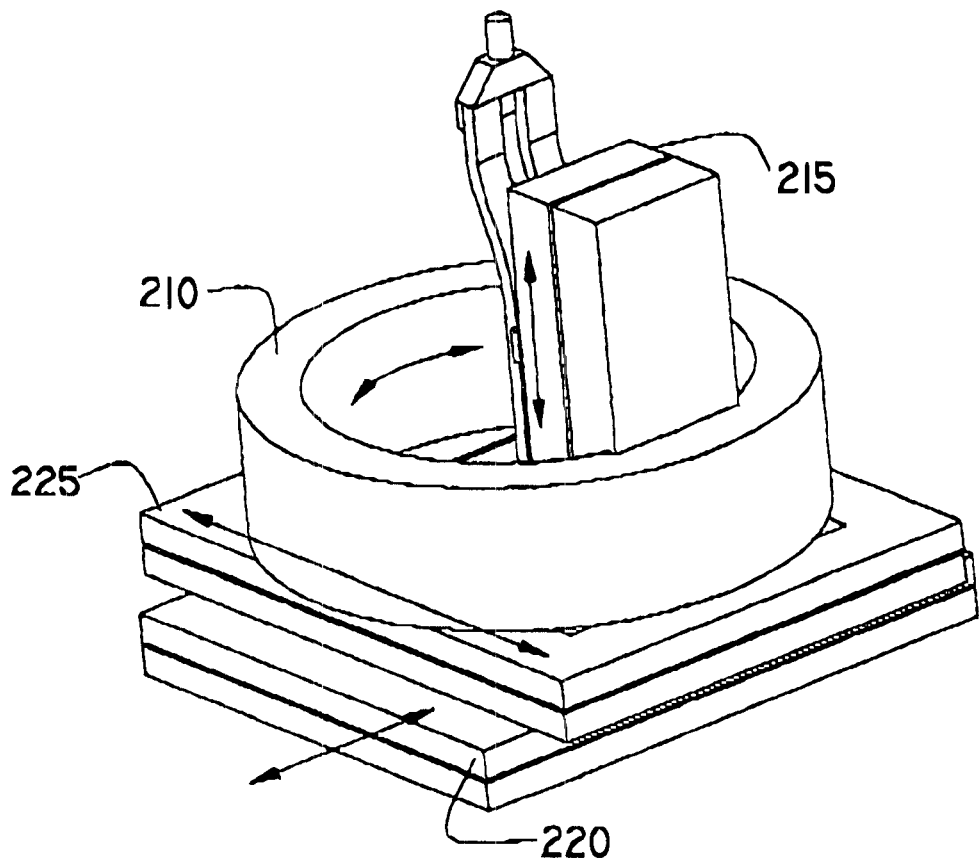
FIG. 6 is an isometric view of a stage for the scanning apparatus of the invention, providing for rotational movement of the scanning apparatus, as well as movement in X, Y and Z axes.

In addition to the scanning motion shown in FIG. 5, several other motions may be produced by the mechanism of the invention to scan an eye. In order to produce various meridian angles theta as shown on FIG. 5, the scan mechanism 10 may rotate about the machine axis 25 (shown in FIG. 4). Rotational motion of the scanning apparatus may be accomplished using rotary table 210. Motion in the Z axis, which shifts the mechanism toward or away from the eye, may be used to compensate for the degree of insetting of a patient's eye. Motion in the Z axis may be accomplished using a Z-slide 215, which may be motorized or manually controllable. Motion along the X and Y axes, perpendicular to the machine axis 25, may be used to adjust the position of the ultrasound scanning apparatus once a patient has been positioned in front of the machine. These motions may be produced by X slide 220 and Y slide 225. In some embodiments, the X and Y slides may be motorized to facilitate X and Y motion of the scanning apparatus in planar scans of eye structures, such as the iris plane. These axes may of course be arranged differently than shown in FIG. 6 while retaining the same essential operation.

Figure 8:
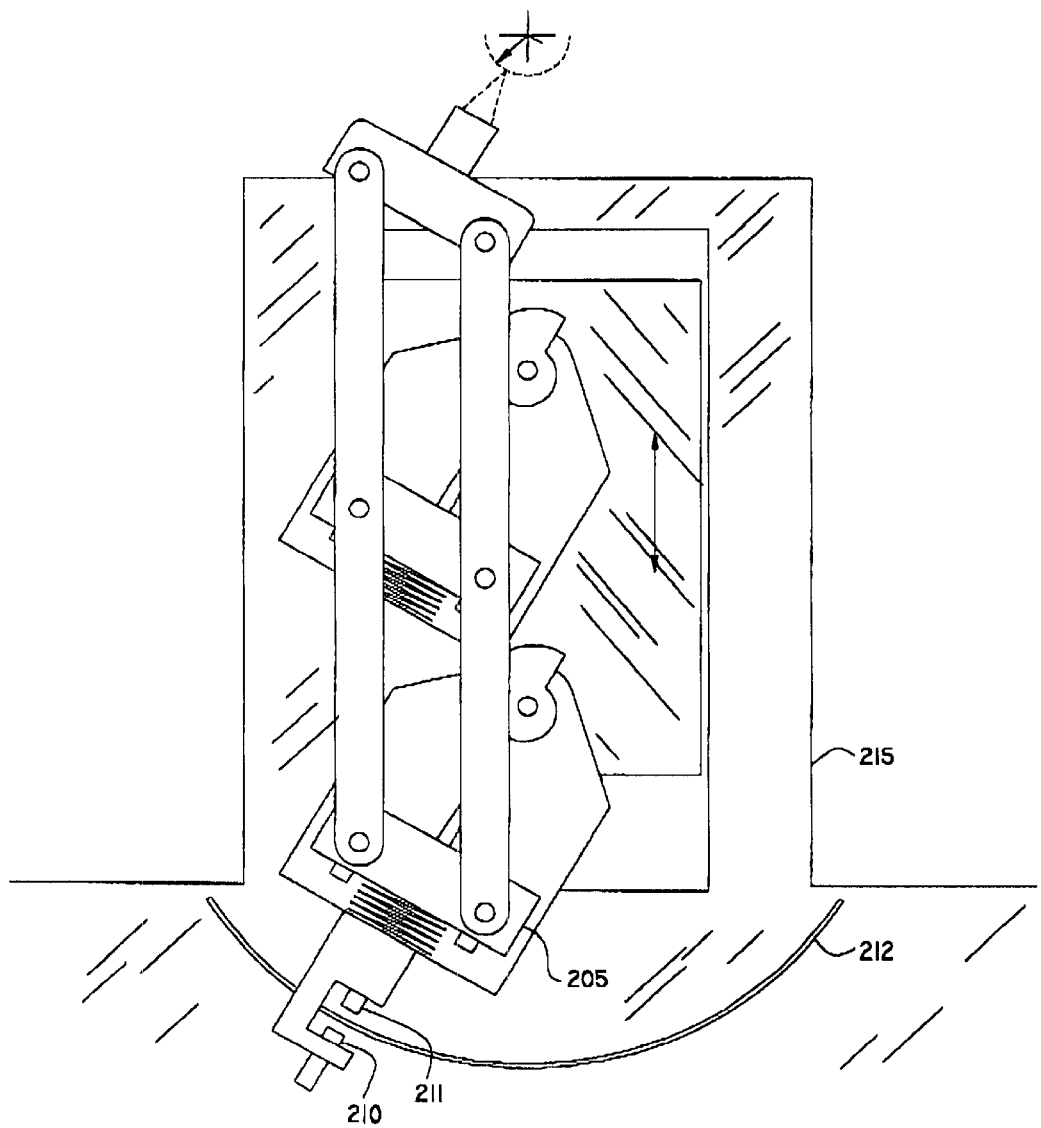
FIG. 8 is an elevational view showing a mechanical safety stop mechanism.

In order to provide a mechanical means of preventing the transducer from approaching an eye too closely, a safety stop as shown in FIG. 8 may be used. The transducer may be shifted closer to the eye by either a radius adjustment or Z axis adjustment. A curved stop bar 212 may be fixed to the body of the Z axis stage 215. Stop pads 210 and 211 are fixed to radius adjust slider 205 so that an excess motion of either the radius or Z axes causes one of the pads to touch the stop bar. These stop pads 210, 211 may be supplemented with sensors for operator feedback.

Figure 7:
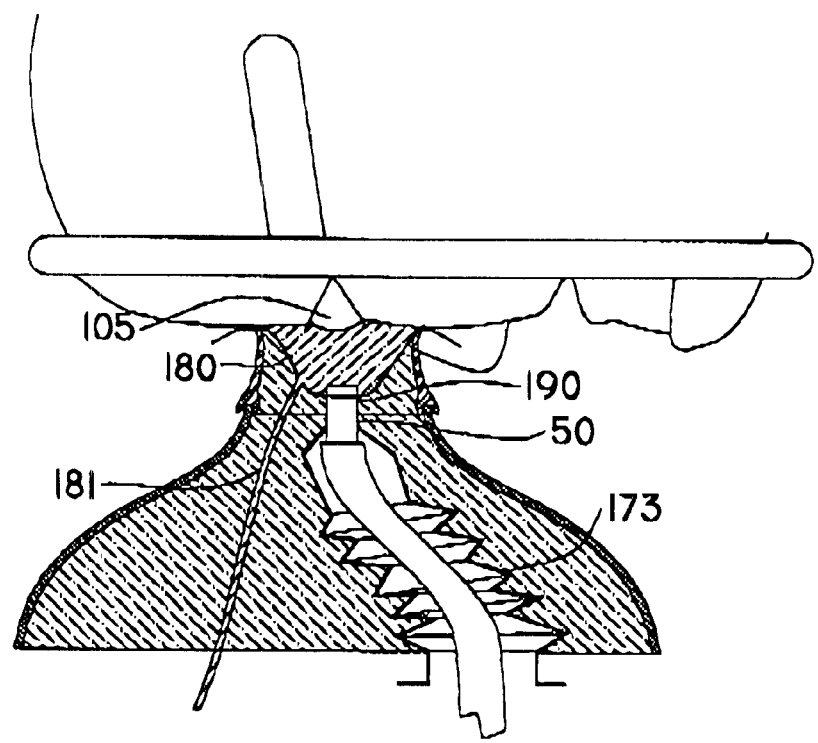
FIGS. 7 and 7A are cross-sectional side views showing a membrane which may be used in some embodiments to isolate a volume of fluid around a patient's eye.
Figure 7A:
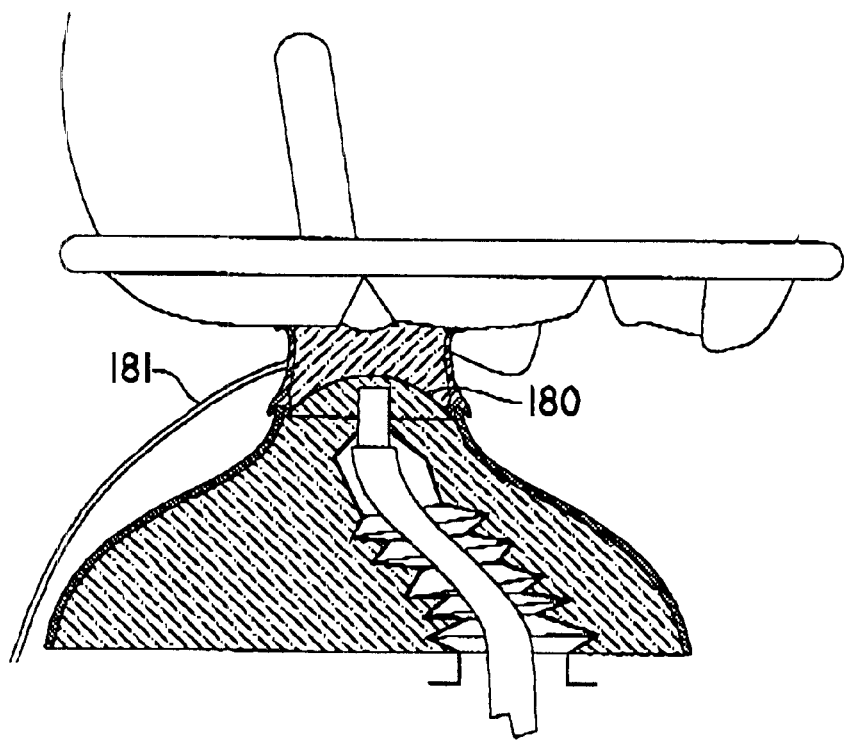

In some embodiments, it may be desirable to provide a barrier to inhibit the passage of an infection from one patient to another. In some embodiments, it will be necessary for the centration light beam and the Purkinje (or other axis) reflections to pass through such a barrier without significant shifting or distortion. In one embodiment, membrane 180 as shown in FIG. 7 may be used, which has saline fluid on both sides of it and is selected to have a similar index of refraction to saline so that light rays passing through membrane 180 will be affected very little by its presence. A filling and draining system may be provided, as shown by tube 181 in FIG. 7. The outer edges of the membrane 180 may be draped over the eye seal and provide the sealing surface for the face. Near its center membrane 180 may be attached by clamp 190 to transducer 50. Clamp 190 may be adapted to accommodate rotation of transducer 50 relative to the eye seal 15 during a scan, for example by permitting rotational movement of transducer 50 within clamp 190. Alternatively, membrane 180 may be continuous, and adapted to permit transmission of ultrasonic vibrations through the membrane itself as shown in FIG. 7A. In some embodiments, bellows seal 173 may be provided over ultrasound transducer 50 and linkage arms 65A, 65B.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

What is claimed is:

1. An ultrasound transducer support comprising:
   a) a transducer mount adapted to accommodate an ultrasound transducer having a focal point;
   b) a virtual center mechanism attached to the transducer mount for moving the ultrasound transducer along an arcuate translation path offset from a virtual center of translocation by a radius of transducer translocation, so that the focal point of the ultrasound transducer traverses an arcuate focal path about the virtual center of translocation; and,
   c) a radius adjust mechanism for adjusting the position of the transducer mount to change the radius of transducer translocation.

2. The ultrasound transducer support of claim 1, wherein the virtual center mechanism comprises:
   a) first and second arm linkages connecting the transducer mount to front and rear swinging linkages, the front swinging linkage being mounted for rotational movement about a front pivot, the rear swinging linkage being mounted for rotational movement about a rear pivot, wherein:
      i) the first and second arm linkages are connected to the transducer mount by transducer pivots;
      ii) the first and second arm linkages are connected to the front swinging linkage by front swinging pivots;
      iii) the first and second arm linkages are connected to the rear swinging linkage by rear swinging pivots.

3. The ultrasound transducer support of claim 2, wherein the front swinging pivots are radially spaced apart equidistant from the front pivot on the front swinging linkage, and the rear swinging pivots are radially spaced apart equidistant from the rear pivot on the rear swinging linkage, so that when the front swinging linkage rotates about the front pivot:
   a) the front swinging pivots traverse a first circular arc which is a first radius from the front pivot;
   b) the rear swinging linkage rotates about the rear pivot so that the rear swinging pivots traverse a second circular arc which is a second radius from the rear pivot; and,
   c) the transducer pivots traverse the arcuate translation path about the virtual center of translocation, the arcuate translation path being offset from the virtual center of translocation by the radius of transducer translocation;

wherein the first radius, the second radius and the radius of transducer translocation are the same magnitude.

4. The ultrasound transducer support of claim 3, wherein the radius adjust mechanism is adapted to simultaneously vary the first radius, the second radius and the radius of transducer translocation, the radius adjust mechanism comprising:
   a) a front radius adjust slider slidably mounted on the front swinging linkage, with the front swinging pivots mounted on the front radius adjust slider;
   b) a rear radius adjust slider slidably mounted on the rear swinging linkage, with the rear swinging pivots mounted on the rear radius adjust slider;

wherein the front and rear radius adjust sliders are operably linked so that sliding movement of the front and rear radius adjust sliders with respect to the front and rear swinging linkages simultaneously changes the first radius, the second radius and the radius of transducer translocation.

5. The ultrasound transducer support of claim 4, wherein the radius adjust mechanism further comprises a cam for actuating sliding movement of the front and rear radius adjust sliders with respect to the front and rear swinging linkages.

6. The ultrasound transducer support of claim 1, wherein the ultrasound transducer is a single element focused transducer.

7. The ultrasound transducer support of claim 1, wherein the arcuate focal path is between the virtual center of translocation and the ultrasound transducer.

8. The ultrasound transducer support of claim 1, wherein the virtual center of translocation is between the arcuate focal path and the ultrasound transducer.

9. The ultrasound transducer support of claim 1, wherein the ultrasound transducer is adjustably mounted in the transducer mount, so that adjustment of the position of the transducer in the transducer mount changes the arcuate focal path.

10. The ultrasound support of claim 1 further comprising centration optics for centring the ultrasound transducer in alignment with an optical or geometric axis of a patient's eye.

11. The ultrasound support of claim 10, wherein the axis of the patient's eye is the Purkinje axis.

12. The ultrasound support of claim 10, wherein the centration optics comprises a centration light source having a centration light beam alignable to intersect the arcuate translation path of the transducer.

13. An ultrasound transducer support comprising:
   a) a transducer mount adapted to accommodate an ultrasound transducer having a focal point;
   b) a virtual center mechanism attached to the transducer mount for moving the ultrasound transducer along an arcuate translation path offset from a virtual center of translocation by a radius of transducer translocation, so that the focal point of the ultrasound transducer traverses an arcuate focal path about the virtual center of translocation
   c) centration optics for centring the ultrasound transducer in alignment with the an optical or geometric axis of a patient's eye wherein the centration optics comprise a centration light source having a centration light beam alignable to intersect the arcuate translation path of the transducer.

14. The ultrasound transducer support of claim 13, wherein the optical or geometric axis of the patient's eye is the Purkinje axis.

15. The ultrasound support of claim 1, further comprising a focus point illuminator adapted to produce a focus spot appropriately positioned on a patient's eye when the ultrasound transducer is a known distance from a patient's eye.

16. A method of ophthamological ultrasonography comprising:
   a) centering an ultrasound transducer having a focal point in alignment with an optical or geometric axis of a patient's eye using centration optics;
   b) moving the ultrasound transducer along an arcuate translation path intersecting the optical or geometric axis of the patient's eye, wherein the arcuate translation path is offset from a virtual center of translocation by a radius of transducer translocation, so that the focal point of the ultrasound transducer traverses an arcuate focal path about the virtual center of translocation.

17. The method of ophthamological ultrasonography of claim 16, wherein the optical or geometric axis of the patient's eye is the Purkinje axis.

* * * * *